(12) United States Patent
Bornet et al.

(10) Patent No.: US 9,173,393 B2
(45) Date of Patent: Nov. 3, 2015

(54) **WATER INSOLUBLE CHITOSAN POWDER AND METHOD OF LIMITING *BRETTANOMYCES* YEAST IN FERMENTED LIQUIDS**

(75) Inventors: Aurélie Bornet, Lucinges (FR);
Sandrine Gautier, Liege (BE);
Véronique Maquet, Berloz (BE);
Pierre-Louis Teissedre, Montpellier (FR); Daniels Granes, Narbonne (FR);
Lucile Pic-Blateyron, Gigean (FR)

(73) Assignee: Kitozyme, Herstal (BE)

( * ) Notice: Subject to any disclaimer, the term of this patent is extended or adjusted under 35 U.S.C. 154(b) by 288 days.

(21) Appl. No.: 13/704,840

(22) PCT Filed: Jun. 16, 2011

(86) PCT No.: PCT/FR2011/051368
§ 371 (c)(1),
(2), (4) Date: Mar. 6, 2013

(87) PCT Pub. No.: WO2011/157955
PCT Pub. Date: Dec. 22, 2011

(65) Prior Publication Data
US 2013/0156836 A1 Jun. 20, 2013

(30) Foreign Application Priority Data
Jun. 18, 2010 (FR) ..................... 10 54887

(51) Int. Cl.
| | |
|---|---|
| *A61K 9/16* | (2006.01) |
| *A01N 43/16* | (2006.01) |
| *A61K 9/51* | (2006.01) |
| *A61K 9/50* | (2006.01) |
| *A01N 25/12* | (2006.01) |
| *A23L 1/056* | (2006.01) |
| *A23L 1/30* | (2006.01) |
| *A23L 2/44* | (2006.01) |
| *A23L 2/52* | (2006.01) |
| *A23L 3/3526* | (2006.01) |
| *A23L 3/3544* | (2006.01) |
| *C08B 37/08* | (2006.01) |
| *C08L 5/08* | (2006.01) |
| *C12G 1/02* | (2006.01) |
| *C12H 1/14* | (2006.01) |
| *B32B 5/16* | (2006.01) |

(52) U.S. Cl.
CPC ............. *A01N 43/16* (2013.01); *A01N 25/12* (2013.01); *A23L 1/056* (2013.01); *A23L 1/30* (2013.01); *A23L 2/44* (2013.01); *A23L 2/52* (2013.01); *A23L 3/3526* (2013.01); *A23L 3/3544* (2013.01); *A61K 9/1652* (2013.01); *A61K 9/5036* (2013.01); *A61K 9/5161* (2013.01); *B32B 5/16* (2013.01); *C08B 37/003* (2013.01); *C08L 5/08* (2013.01); *C12G 1/02* (2013.01); *C12H 1/14* (2013.01); *A23V 2002/00* (2013.01); *C12G 2200/21* (2013.01); *Y10T 428/2982* (2015.01)

(58) Field of Classification Search
CPC ............ A61L 2300/34; A61K 9/1652; A61K 9/5036; A61K 9/5161
See application file for complete search history.

(56) References Cited

U.S. PATENT DOCUMENTS

| 6,482,456 B1 | 11/2002 | Yokoo et al. |
| 2004/0176477 A1 | 9/2004 | Davison et al. |

FOREIGN PATENT DOCUMENTS

| FR | 1164984 | 10/1958 |
| FR | 2599048 | 11/1987 |

OTHER PUBLICATIONS

International Search Report of the International Searching Authority mailed Dec. 5, 2012, issued in connection with International Patent Appln. No. PCT/FR2011/051368 (7 pages).
Gomez-Rivas, et al., "Selective Antimicrobial Action of Chitosan Against Spoilage Yeasts in Mixed Culture Fermentations," Journal of Industrial Microbiology and Biotechnology, vol. 31, No. 1 (2004) (7 pages).
Written Opinion of the International Searching Authority Mailed Mar. 5, 2013, issued in connection with International Patent Application No. PCT/FR2011/051368 (English Translation) (27 pages).
Chun, et al., "Research on the Application of Chitosan in the Clarification of White Wine," with English translation of Abstract (2006) (3 pages).

*Primary Examiner* — Carlos Azpuru
(74) *Attorney, Agent, or Firm* — McCarter & English, LLP

(57) ABSTRACT

The invention relates to a chitosan as a micronized powder, to its use for controlling certain yeasts, such as *Brettanomyces*, and to a method for treating a liquid food.
The invention in particular relates to a water-insoluble chitosan as a micronized powder, for which the grain size is comprised between 5 and 50 microns, and to its use in the treatment of liquid foods and/or for controlling *Brettanomyces*.

24 Claims, 5 Drawing Sheets

WATER INSOLUBLE CHITOSAN POWDER AND METHOD OF LIMITING *BRETTANOMYCES* YEAST IN FERMENTED LIQUIDS

RELATED APPLICATIONS

This application is a U.S. National Phase Application under 35 U.S.C. 371 of International Application No. PCT/FR2011/051368 filed Jun. 16, 2011, which was published on Dec. 22, 2011 under International Publication Number WO 2011/157955 A2, which claims the benefit of French Patent Application No. 1054887 filed on Jun. 18, 2010. These applications are incorporated herein by reference in their entirety.

The invention relates to a chitosan in the form of a fine and controlled powder, its use for controlling certain yeasts like *Brettanomyces* and to a method for treating a liquid food.

STATE OF THE ART

The *Brettanomyces* are described as an agent which contaminates many fermentation products including wine, cider, beer, kombucha, kefir, tequila, etc., In the wine-producing sector, detection of contamination yeasts in the vineyard becomes delicate by the fact that they are a minority at this stage. However, fermentation (process for transforming sugars into alcohol) will cause a real « selection » of these microorganisms. Indeed, *Brettanomyces* are particularly resistant to ethanol and to $SO_2$ and are capable of subsisting in the medium in spite of its depletion in sugars. Further, certain techniques or certain procedures for making wine may promote development of *Brettanomyces* in wine, such as maturation on lees. In order that the *Brettanomyces* may develop, less than 500 mg of sugar are sufficient for them.

The impact of the *Brettanomyces* contamination yeasts has been proved by many authors on wines in different countries, in German sparkling wines, Arbois « vins jaunes » (yellow wines), or wines from the South of France. In 1965, Domercq reported the isolation of *Brettanomyces* in musts of the wine origin labels « Saint Emilion » and « Premières Côtes de Bordeaux » and in red or white wines being kept of the wine origin labels « Medoc », « Graves » and « Saint-Emilion ». As for the types of vine, pinot seems to be the most affected. In Burgundy, for example, for the 2000 vintage, 50% of the fermenting wines from this type of vine and 25% of them after bottling have been affected.

Eventually, the control of this alteration remains difficult, even with careful consideration of oenological practices. The control means are essentially preventive, they give the possibility of acting on populations of *Brettanomyces* ($SO_2$, DMDC, flash pasteurization, filtration). However these treatments modify the organoleptic properties of the wines and do not preserve the treated wines from subsequent contaminations.

This problem is not only associated with wines, but extends to liquid food of vegetable orig in notably prepared by fermentation.

Chitosan is known as a technological auxiliary, but its used in solution requires high concentrations, generally of the order of 30 to 100 g/hL. On the other hand, the antibacterial and antifungal properties of chitosan have been widely studied and documented and are today well recognized. Chitosan is known for its antimicrobial effect within a relatively short time, when it is used in solution with organic acids, generally at an acid pH, at concentrations of the order of 0.5 to 1.5% (i.e. concentrations of 0.5 g/100 mL, 5 g/L, 500 g/hL to 1,000 g/hL). These concentrations are high since in most cosmetic, food or medical applications, a wide inhibition spectrum (bacteria, yeasts) is needed.

In the same way, the antifungal activity of chitosan towards various fungi except those containing chitosan as a substantial component of their cell wall is also described. Chitosan in solution was studied for controlling phytopathogenic strains (*Fusarium, Rhizopus, Phylium, Candida, Aspergillus*). Chitosan in solution was also studied on the growth of *Saccharomyces cerevisiae* and lactic bacteria (*Pediococcus* and *Lactobacillus*) during fermentation. The authors demonstrate that chitosan inhibits in a more marked way the growth of *Saccharomyces cerevisiae* than lactic bacteria (*Pediococcus* and *Lactobacillus*).

The fungicidal action of chitosan in the form of microparticles having a size of less than 5 µm is described by Allan C. et al. (Allan C. et al., (1979) The fungicidal effect of chitosan on fungi of varying cell wall composition Experimental Mycology, 3: 285-287) in laboratory tests aimed at measuring inhibition of the growth of microorganisms in the presence and in the absence of chitosan. The concentrations of use are high (0.1 to 6 g/L). No data is provided concerning the action against *Brettanomyces*. Further the authors have observed that the response variability and the sensitivity to chitosan strongly depends on the genus and the species.

Gomes-Rivas et al. (Gomes-Rivas L. et al., (2004) Selective antimicrobial action of chitosan against spoilage yeasts in mixed culture fermentations, J. Int Microbial Biotechnol 31:16-22) describes the action of chitosan for specifically controlling the genus *Brettanomyces/Dekkera*. However the authors describe the effect of chitosan in the form of a fine powder of microparticles having a size of less than 420 µm, DA 9%; DA=degree of acetylation) on the growth of *Brettanomyces bruxellensis* and on that of *Saccharomyces cerevisiae*. The tests are conducted on a culture medium. The effect is therefore not measured on the wine matrix which randomizes any conclusion on the use of such a chitosan as a technological auxiliary. The authors indicate that the growth of the *B. bruxellensis* is inhibited during the first 80 hours of the treatment with chitosan and that growth resumes beyond this latency period. They show that with chitosan at 600 g/hL it is possible to control the growth of *B. bruxellensis*. This concentration therefore remains very high for suitable industrial use.

Patent application US 2004/0176477 describes a water-soluble micronized chitosan, used as an antimicrobial agent towards *Malassezia furfur* and *Staphylococcus epidermis*.

Patent application FR 2 599 048 teaches according to the examples that it is possible to use a chitosan concentration of about 80 g per hectoliter of liquid food for stabilizing this liquid food, notably from the point of view of its color. This chitosan concentration remains high.

U.S. Pat. No. 6,482,456 describes an aqueous solution of chitosan, i.e. water-soluble chitosan.

Patent application FR 1 164 984 teaches the use of chitosan in a mixture with bentonite when the amount of chitosan has to be reduced for clarification of pressed juices.

As already mentioned, in its cationic form, chitosan is provided with antimicrobial activity on certain strains. The presence of functional groups which may easily be substituted allows modification of the properties of chitosan and therefore of its activity.

For example chitosan glutamate or lactate in solution has already been used for limiting an antimicrobial or antifungal action.

However, the chitosan proposed to this day is not used as a technological auxiliary in order to meet the expectations of the professionals of this industry for preventing the « *Brettanomyces* risk».

OBJECTS OF THE INVENTION

This is why Kitozyme SA has set up a research and development program in order to find a technological auxiliary solving the technical problems described above and below.

The main object of the invention is to solve the novel technical problem consisting in providing a technological auxiliary, for controlling yeasts of the *Brettanomyces* genus.

The object of the invention is also to solve the novel technical problem consisting in providing a technological auxiliary for controlling undesirable yeasts in a liquid food, and in particular a liquid food prepared by fermentation, and notably yeasts of the *Brettanomyces* genus.

The object of the invention is also to provide a useable technological auxiliary, reliable from the point of view of food safety and not degrading the quality of the treated liquid foods.

The object of the invention is to solve these technical problems on an industrial scale, notably for the industry of liquid foods, optionally with alcohol or fermented.

DESCRIPTION OF THE INVENTION

Figure 1:
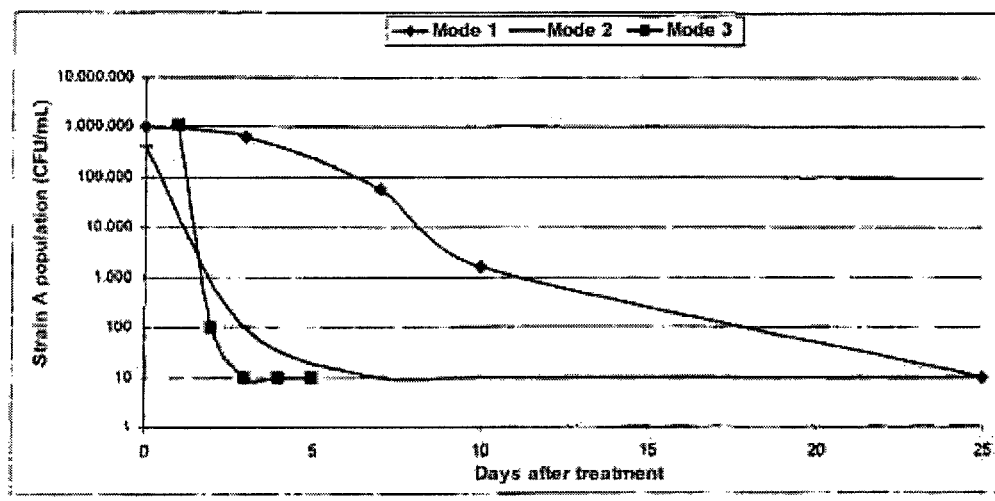
FIG. 1 is a graph tracking the *Brettanomyces bruxellensis* strain A population in a wine after treatment with chitosan.

Thus, the present invention relates to a chitosan in the form of a powder for which the grain size (particle diameter) is comprised between 0.1 and 200 µm.

Advantageously, the chitosan comprises a grain size comprised between 5 and 100 microns, and preferably between 5 and 60 microns, and still preferably comprised between 5 and 50 microns.

According to an alternative, the chitosan comprises a grain size of less than 70 microns, and preferably less than 50 microns.

Surprisingly, with a powder having a grain size of less than 100 microns, it is possible to obtain a very significant and very rapid effect on the population of undesirable yeasts. This effect is particularly marked when the grain size is less than 50 microns.

The grain size is the one obtained by laser diffractometry.

The chitosan of the invention preferably has a grain size having a D(0.5) (mean diameter of the total distribution with 50% of the volume of particles which have a diameter of less than this value and 50% have a greater diameter) comprised between 5 and 30 µm, preferably between 10 and 30 µm and more preferably between 10 and 25 µm. D(0.5) therefore represents the middle of the distribution taking into account the areas under the distribution curve of the grain size.

According to an alternative, the chitosan may be used after sifting.

Preferably, the chitosan comprises an acetylation degree (DA) comprised between 0 and 30 mol %. The degree of acetylation is the ratio of the number of N-acetyl-glucosamine units over the number of total monomers. The degree of acetylation of chitosan is determined by potentiometric titration which consists of determining the degree of acetylation of chitosan by titration of the amine groups. This is based on the work of Rinaudo et al., (1999). Briefly, chitosan is put into solution in an excess of diluted hydrochloric acid. The amine groups (on the non-acetylated glucosamine units (G)) are positively charged (excess HCl). The solution is then titrated with a diluted NaOH solution, by means of an automatic titrator (KEM, automatic potentiometric titrator, AT-500N) and the pH is measured. In the first part of the reaction, the excess amount of HCl is determined. Next, the amount of charged amine groups is determined:

The titration curve shows two inflection points. The difference between both NaOH volumes gives the possibility of knowing the amount of free amines.

Chitosan is referenced under CAS No. 9012-76-4. The chitosan of the invention is a polysaccharide prepared from a fungal origin. It is extracted and purified from secure and abundant biotechnological or food fungal sources such as *Agaricus bisporus* or *Aspergillus niger*. The chitosan is obtained by hydrolysis of a chitin-rich extract. Chitin is a polysaccharide consisting of several N-acetyl-D-glucosamine units bound together through a bond of the β type (1,4). The chitosan consist of glucosamine sugar units (deacetylated units) and of N-acetyl-D-glucosamine units (acetylated units) bound together through bonds of the β type (1,4) and form a polymer of the poly(N-acetyl-D-glucosamine)-poly(D-glucose) type. In the invention, the percentage of glucans (D-glucose units) is preferably less than 15% (mass/mass) of the polymer.

The chitosan of the invention is useful as a technological auxiliary. By technological auxiliary is meant a substance or material excluding any apparatus or instrument, which is not consumed as a food ingredient per se, which is intentionally used in the transformation of raw materials, foodstuffs or their ingredients, for meeting a certain technological goal during the treatment or the transformation and which may have the result of a non-intentional but inevitable presence of residues or foodstuffs in the finished product (definition from the CODEX Alimentarius).

The chitosan of the invention is advantageously of fungal original and preferably stems from the mycelium of a fungus of the *Ascomycetes* type, and in particular from *Aspergillus niger*, and/or from a fungus *Basidiomycetes*, and in particular

*Lentinula edodes* (shiitake) and/or *Agaricus bisporus*. Preferably, the fungus is *Aspergillus niger*. The chitosan may be of GMO origin but preferably it is of non-GMO origin. Any type of chitosan may be used. A method for preparing chitosan is the one described in patents WO03068824 (EP1483299; U.S. Pat. No. 7,556,946).

Many studies demonstrate that the antimicrobial activity of chitosan varies according to the degree of acetylation (DA) and to the molecular weight (Molecular Weight: MW) of the chitosan. The invention thus covers the different DA and MW ranges.

Both parameters (DA and MW) affect the antimicrobial activity of chitosan, independently, however it would seem that the influence of MW is more important on the antimicrobial activity than the influence of DA (Sekiguchi, S., et al. (1994) *Molecular weight dependency of antimicrobial activity by chitosan oligomers*, in: Nishinari, K. & Doi, E. (Eds), "Food Hydrocolloids: Structures, Properties and Functions", Plenum Press, New York).

In order to cite recent examples, studies carried out on bacteria, notably including those by Omura, Y., et al. (Omura, Y., et al. (2003) Antimicrobial activities of chitosan with different degrees of acetylation and molecular weights Biocontrol. Sci., 8(1): 25-30); Tsai, G. J.; Zhang, S. L., Shieh, P. L. (Tsai, G. J. et al. (2004) Antimicrobial Activity of a Low-Molecular-Weight Chitosan Obtained from Cellulase Digestion of Chitosan J. Food Prot., 67(2): 396-398); Zivanovic S., et al. (Zivanovic S. et al., (2004) Molecular Weight of Chitosan Influences Antimicrobial Activity in Oil-in-Water Emulsions J. Food Prot., 67(5): 952-959.

For the fungi, Eaton, P. et al. (Eaton, P. et al., (2008) Atomic force microscopy study of the antibacterial effects of chitosans on *Escherichia coli* and *Staphylococcus aureus* Ultramicroscopy, 108 (10): 1128-1134.) have found that the lower the molecular weight (MW) of chitosan, better is the inhibiting effect of chitosan on growth and multiplication of microorganisms.

In the same way, many studies have demonstrated an inverse relationship between the DA of chitosan and its antimicrobial activity (Hongpattarakere, T., et al. (2008) Effect of deacetylation conditions on antimicrobial activity of chitosans prepared from carapace of black tiger shrimp (*Penaeus monodon*) Songklanakarin J. Sci. Technol., 30(1): p. 1-9; Tsai, G. J., and al. (2002) Antimicrobial activity of shrimp chitin and chitosan from different treatments Fisheries Sci., 68 (1): 170-177).

The invention also relates to a composition comprising a chitosan as defined earlier.

In particular, the invention relates to a chitosan suspension of the invention. More particularly, this suspension is adapted for a use as a technological auxiliary, for example from the point of view of its qualitative composition, of its purity and/or of the chitosan source.

The chitosan is incorporated as a powder into the liquid food to be treated. It is notably used with view to microbiological stabilization by eliminating *Brettanomyces*.

The chitosan of the invention is therefore insoluble in water. By « insoluble in water » is meant a chitosan for which at least 90%, and preferably 95% (mass/mass), is not soluble in distilled water. In the examples, as the chitosan is considered to be totally insoluble, the percentage of the soluble materials in water may be assimilated to impurities.

The chitosan of the invention is insoluble, has a crystalline portion, generally of more than 2% (mass/mass) after hydration.

Before its use as a technological auxiliary, the chitosan is suspended and mixed in a liquid (like for example water) compatible with the liquid food to be treated, i.e. which is not detrimental to the final use of the liquid food. The chitosan/liquid mass ratio (for example: chitosan/water) is preferably comprised between 1/1 and 1/10 and is preferably of 1/5 (mass/mass; m/m). Chitosan does not dissolve in water, therefore the mixture has to be well stirred beforehand. Preferably the mixture is stirred just before adding it to the liquid to be treated.

The chitosan or chitosan suspension of the invention is added to the liquid food to be treated. The chitosan should also be homogeneous over the whole of the volume of liquid to be treated and for example during pump-over by pouring the product with small volumes, in order to ensure good distribution into the bulk of the wine. The chitosan should therefore be added gradually. It is preferable to homogenize the liquid to be treated at the same time as the addition of chitosan. For treating a wine, the complete pump-over of the vat is generally required. At the end of the treatment, the chitosan (technological auxiliary) is removed by drawing-off in order to remove the chitosan and the absorbed microorganisms. This removal step is for example carried out after an action time from 7 days to 10 days and after natural decantation of the liquid to be treated, and typically in the treatment of a fermented liquid food such as wine.

The invention also relates to the use of chitosan or of a composition as defined earlier, as an antifungal agent, and notably for controlling yeasts, in particular the yeasts *Brettanomyces* and/or *Dekkera*, and even more particularly the yeasts *B. anomalus, B. bruxellensis, B. claussenii, B. custersianus, B. lambicus, B. naardenensis*, and/or *B. nanus*. The action of the chitosan of the invention is not limited to a particular strain since several strains of the same type were tested. As indicated earlier, the known concentrations of chitosan of the prior art are high since in most cosmetic, food or medical applications, a wide inhibition spectrum is needed (bacteria, yeasts). Now this effect is not sought in the present invention, on the contrary, inhibition of useful bacteria and yeasts for example during fermentation like in wine-making for example must be avoided. The invention is therefore surprising since at a very low dose (<10 g/hL), the chitosan of the invention selectively acts on the undesirable yeasts.

On the other hand, the invention relates to the use of chitosan or of a composition as defined earlier, as an antifungal agent, and notably for controlling undesirable yeasts in a liquid food, and notably of vegetable origin, i.e. prepared from plants (grapes, apples, potatoes, beetroots, etc.), and in particular a liquid food prepared by fermentation, for example wine, beer, cider, sparkling wine, or fruit juice. The invention relates to the treatment of liquid food such as water, fermented drinks (drinks obtained by transformation of foods in solution into alcohol, by fermentation of the basic products), liqueur wines (a must in which an alcohol is added), spirits (obtained by distillation of fermented drinks) the most common liqueur wines are: Pineau des Charentes (based on Cognac), Floc de Gascogne (based on Armagnac), Ratafia of Champagne and Burgundy, Riquiqui, Macvin from the Jura, Cataroise from Beziers, Pommeau from Normandie (based on Calvados). The liquid foods may be obtained from different parts of plants: leaves, roots, cereals, fruit, etc. The invention therefore relates to all liquid foods, including all liquids which may be contaminated by undesirable yeasts of the *Brettanomyces* type; liquids from fermentation (either food or not), such as must before fermentation or during fermentation, or a fermented liquid (for example must/biomass from vegetables—potatoes, beetroots, . . . or grapes); non-fermented liquid foods of vegetable origin (fruit juices), and liquid foods from the fermentation of grape musts.

The treatment of the invention may therefore be applied to Pisco, Pineau des Charentes, spirits, cider, beer, alcohol for industrial purposes and wine.

Surprisingly, it was discovered that the chitosan of the invention may be used as an antifungal agent against undesirable yeasts in a liquid food, and notably of vegetable origin, optionally fermented, which is generally complex from the point of view of its composition. The capability of chitosan of removing yeasts, notably those of the genera or species cited above within a liquid vegetable food, furthermore obtained or still fermenting, was not predictable.

According to another aspect, the invention relates to a method for curative and/or preventive treatment of a liquid food, and notably of vegetable origin, and in particular a liquid food of vegetable origin prepared by fermentation, wherein undesirable yeasts are to be removed, the presence of which should be prevented, and/or the population of which should be limited, and in particular yeasts of the *Brettanomyces* and/or *Dekkera* genus, even more particularly the yeasts *B. anomalus*, *B. bruxellensis*, *B. claussenii*, *B. custersianus*, *B. lambicus*, *B. naardenensis*, and/or *B. nanus*, said method comprising the putting of the liquid food in the presence of a chitosan or a composition as defined earlier.

The invention also relates to a hygiene and prevention method in production premises (production factory, wine and spirit stores, etc) with which it is notably possible to avoid stopping of production for cleaning. The preventive use is generally as important (preventive hygiene of the wine and spirit store of the factory), as the curative treatment.

The liquid food to be treated according to the invention is in particular a wine, a beer or a cider.

The undesirable yeasts are notably *B. anomalus* and/or *B. bruxellensis*. The invention in particular relates to a method for treating a liquid food, optionally fermented, in order to fight against the presence of yeasts of the *Brettanomyces* genus, and in particular of the *Brettanomyces bruxellensis* species.

According to a preferred alternative, the chitosan is present at a concentration from 1 to 10 g/hL of liquid food to be treated, and preferably comprised between 2 and 5 g/hL of liquid food to be treated. The concentration used is therefore particularly low as compared with the other products of the prior art, which often require more than 20 g/hL like for treatment with dimethyl dicarbonate (DMDC).

The liquid food is put into the presence of chitosan for a sufficient period of time for removing, limiting or preventing the presence of yeasts, notably of the yeast described above. This period of time is generally of at least 3 days, and preferably of at least 5 days and still preferably of at least 7 days.

By « removing » the presence of the yeasts, is meant the fact of reducing the population of undesirable yeasts below the detection threshold (10 CFU/mL). By « limiting » , is meant limiting the population by at least a factor 10 or even 100 of undesirable yeast population. By « preventing » is meant preventing the development, the proliferation and/or limiting the population of undesirable yeasts.

The treatment may be carried out on a liquid food during fermentation. Indeed, it was surprisingly discovered that the chitosan of the invention allows continuation of fermentation, and notably an alcoholic and/or malolactic fermentation. The fermentation is not perturbed by the presence of the chitosan of the invention. The chitosan of the invention notably has no harmful effect on a population of *Saccharomyces cerevisiae*.

The chitosan and/or the composition comprising the chitosan, is preferably separated, for example by drawing-off, fining, filtration and/or centrifugation of the liquid food in order to preserve the liquid food. The liquid food may be drawn off after a sufficient contact time with the chitosan of the invention.

Other objects, features and advantages of the invention will become clearly apparent to one skilled in the art after reading the explanatory description which references examples which are only given as an illustration and which cannot by any means limit the scope of the invention.

The examples are an integral part of the present invention and any feature appearing to be novel relatively to any prior state of the art from the description taken as a whole, including examples, is an integral part of the invention in its function and in its generality.

Thus, each example has a general scope.

On the other hand, in the examples, all of the percentages are given by weight, unless indicated otherwise, and the temperature is expressed in degrees Celsius except if indicated otherwise, and the pressure is atmospheric pressure, unless indicated otherwise.

EXAMPLES

A—The Yeast Strains

The strains of *Brettanomyces bruxellensis* used for artificial inoculation of the wine are strains identified as being a majority on the Mediterranean vine yards and have a 100% A and 100% B genotypes. They stem from the collection of ICV-DNA$^{id}$ strains. They are kept at 4° C. on a tilted gelose medium (YAC medium) after 7 days of incubation at 28° C.

B—The Medium and the Conditions for Cultivation of the Leaven

The leaven is an acclimatization medium in which the yeasts may grow and reach a population of the order of $10^7$ CFU/mL, while being adapted to a not very favorable environment (acid pH, high ethanol content).

The composition of the leaven used for the experiments is described in the following Table 1:

TABLE 1

Composition of the leaven medium for *Brettanomyces bruxellensis*

| Compounds | Concentrations/conditions |
|---|---|
| Yeast Nitrogen Base | 6.7 g/L |
| Glucose | 20 g/L |
| Ethanol | 10% (v/v) |
| Demineralized water | Complete the desired volume |
| pH | Adjust to 3.5 with tartaric acid crystals |
| Sterilization | 20 mins at 121° C. |

C—Analytical Counting Techniques

The counting of viable *Brettanomyces* is accomplished by cultivation on a specific gelose medium YAC (YEPD+Actidione+Chloramphenicol) according to the following procedure: the samples are taken and diluted in cascade under a sterile environment, in tubes containing 9 ml or 9.9 mL of sterile physiological water. 100 µl are cultivated by spreading on a YAC gelose medium, from the suitable dilution in order to have between 30 and 300 colonies on the gelose. The dishes are incubated at 28° C. for 10 days. The cultivations are doubled.

D—Micronization of Chitosan

The chitosan is obtained by extraction and deacetylation (hydrolysis of N-acetyl-glucosamine groups) while starting from the mycelium of *Aspergillus niger* by action of soda. After several washing and purification steps, the chitosan is then dried and milled so as to attain the desired grain size. It is also possible to use a water-insoluble chitosan commercially available in order to then micronize it. The resulting micronized chitosan should be insoluble in water according to the invention.

The micronization of the chitosan stemming from a fungal source (Aspergillus niger) is achieved by means of a milling machine with opposite air jets. Different brands and models of equipment may be used depending on the amount of powders to be treated: for example equipment of the Hozokawa—Alpine brand (model 200 AFG) for amounts >200 kg, and for example equipment of the Netzsch—Model CGS 10 for smaller amounts.

The powder is milled continuously until the micronized powder is passed through a selection turbine for obtaining a powder for which the particles have a diameter of less than 100 μm; or even 50 μm. Grain size analysis of the powder is then carried out with a laser diffractometer Laser Mastersizer 2000 from Malvern Instruments Ltd.

The D(0.50) is comprised between 10 and 30 μm and preferably between 10 and 25 μm, or even between 10 and 20 μm.

E—Characteristics of the Batches of Chitosan Used in Examples 1-26

TABLE 1

| Example | DA (mol %) | Grain size (by laser diffractometer) | Grain size (by sifting) | Chitosan content (%)* | Residual glucans (%) |
|---|---|---|---|---|---|
| 2.3 | 22 | ND | <50 μm | 89.6 | 6.7 |
| 1.1 | ND | ND | ND | ND | ND |
| 1.2, 10-15 | 4.2 | <50 μm; D(0.5): 13.6 μm | ND | 87 | 5.2 |
| 4 | 22 | ND | <25 μm, <50 μm, <90 μm | 89.6 | 6.7 |
| 5 | 22 | ND | ND | 89.6 | 6.7 |
|  | 8.5 |  |  | 90.8 | 7.6 |
| 6.1 | 8.5 | ND | <25 μm, <90 μm | 90.8 | 7.6 |
| 6.2 | 22 | ND | <25 μm, <90 μm | 89.6 | 6.7 |
| 7-9; 16 | 22 | ND | <50 μm | 89.6 | 6.7 |
| 17 | 4.2 | D(0.5): 13.6 | <50 μm | 87 | 5.2 |
| 18 | 4.2 | D(0.5): 13.6 | <50 μm | 87 | 5.2 |
| 19 | 14.30 | D(0.5): 14.1 | <50 μm | 87 | 10.86 |
| 20 | 11.80 | D(0.5): 14.0 | <50 μm | 90 | 8.3 |
| 21 | 11.80 | D(0.5): 14.0 | <50 μm | 90 | 8.3 |
| 22 | 12.47 | D(0.5): 13.6 | <50 μm | 88 | 10.21 |
| 23 | 14.49 | D(0.5): 11.2 | <50 μm | 87 | 7.77 |
| 26 | 11.80 | D(0.5): 14.0 | <50 μm | 90 | 8.3 |

*calculated by subtracting the ashes, proteins and glucans from the weight of the dry sample.
ND: Not determined.
A certain percentage of residual glucans subsists in the chitosan..

Example 1.1

Treatment of a Red Wine Contaminated by Brettanomyces bruxellensis with Chitosan at Different Doses (Laboratory Test)

A finished Medoc wine (Merlot) of vintage 2006 having an initial population level of Brettanomyces bruxellensis de 2.8 $10^5$ cellules/mL was treated by adding chitosan at different doses.

TABLE 2

Quantitative PCR counting of Brettanomyces bruxellensis 7 days after treatment

| Treatment dose | Control | 0.2 g/hL | 0.5 g/hL | 0.7 g/hL | 1 g/hL | 2 g/hL | 5 g/hL |
|---|---|---|---|---|---|---|---|
| Brettanomyces count | 2.8 $10^5$ | 3563 | 1527 | 509 | 254 | 0 | 0 |

After 7 days of treatment, chitosan at a dose of 2 g/hL enables total removal of the Brettanomyces bruxellensis present in the wine.

Example 1.2

Treatment of a Red Wine Contaminated by Brettanomyces intermedius with Chitosan at Different Doses (Laboratory Test)

A finished wine of vintage 2009 having an initial propagation level of Brettanomyces intermedius of 3.7 $10^6$ cells/mL was treated by adding chitosan (DA≈4.2 mol %) at different doses. The control wine does not undergo any treatment.

TABLE 3

Quantitative PCR count and on a specific gelose medium, of Brettanomyces intermedius 10 days after treatment

| Treatment dose | Control | 0 g/hL | 2 g/hL | 3 g/hL | 4 g/hL |
|---|---|---|---|---|---|
| Brettanomyces count (q-PCR) | 3.7 $10^6$ | 8.8 $10^6$ | 2.3 $10^2$ | 1.0 $10^3$ | 30 |
| Brettanomyces count (gelose medium) | 1.1 $10^6$ | 1.8 $10^6$ | 30 | <1 | 1 |

After 10 days of treatment, chitosan enables a significant reduction of the Brettanomyces intermedius present in the wine, at a dose of 4 g/hL.

Example 2

Treatment of a Red Wine Contaminated by Brettanomyces bruxellensis Strain A with Chitosan at a Dose of 4 g/hL (Laboratory Test)

A finished wine from Languedoc Roussillon (Merlot) of vintage 2008 having an initial population level of Brettanomyces bruxellensis strain A of $10^6$ cells/mL was treated by adding chitosan at a dose of 4 g/hL or by adding DMDC at a dose of 20 g/hL. The control wine does not undergo any treatment.

FIG. 1—Tracking the Brettanomyces bruxellensis strain A population in the wine after treatment
Caption—
Mode 1: Control;
Mode 2: Treatment with 20 g/hL DMDC;
Mode 3: Treatment with 4 g/hL chitosan It is seen that the treatment with chitosan (Mode 3) is as efficient as the treatment with DMDC (mode 2) towards Brettanomyces bruxellensis strain A. Indeed, a sufficient reduction of the Brettanomyces bruxellensis strain A population (≤10 CFU/mL) is seen within 5 to 10 days with both types of treatment.

Example 3

Treatment of a Red Wine Contaminated by Brettanomyces bruxellensis Strain B with Chitosan at a Dose of 4 g/hL (Laboratory Test)

A finished wine from Languedoc Roussillon (Merlot) of vintage 2008 having an initial population of *Brettanomyces bruxellensis* strain B of $10^5$ cells/mL was treated by adding chitosan at a dose of 4 g/hL or by adding DMDC at a dose of 20 g/hL. The control wine does not undergo any treatment.

Figure 2:
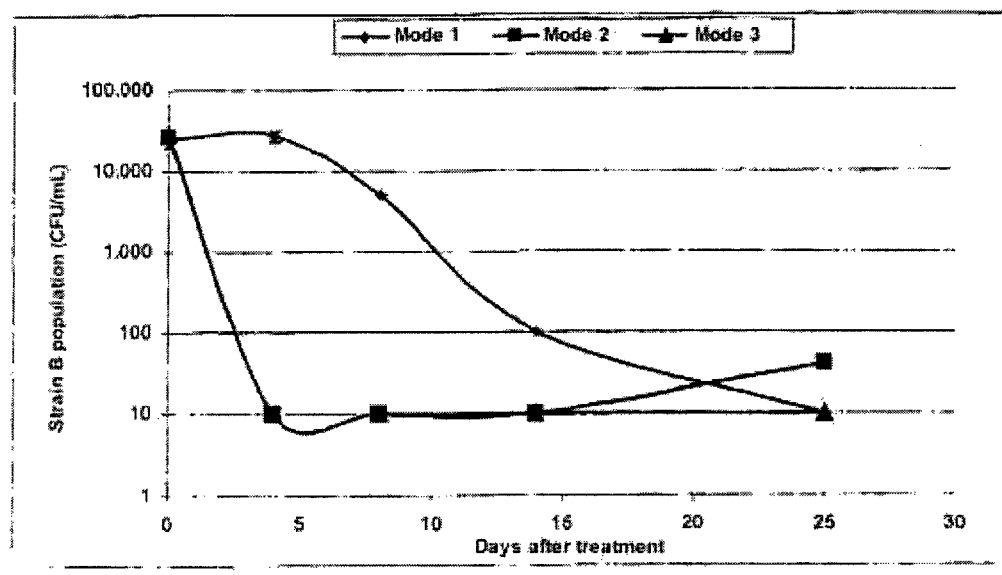
FIG. 2 is a graph tracking the population of *Brettanomyces bruxellensis* strain B in a wine after treatment with chitosan.

FIG. 2—Tracking the population of *Brettanomyces bruxellensis* strain B in the wine after treatment Caption—
Mode 1: Control;
Mode 2: Treatment with 20 g/hL DMDC;
Mode 3: Treatment with 4 g/hL chitosan It is seen that the treatment with chitosan (mode 3) is as efficient as the treatment with DMDC (mode 2) towards *Brettanomyces bruxellensis* strain B. Indeed, a significant reduction in the population of *Brettanomyces bruxellensis* strain B is seen (≤10 CFU/mL) within 5 to 10 days with both types of treatment.

Example 4

Treatment of a Red Wine Contaminated by Brettanomyces bruxellensis with Chitosan of Different Grain Sizes at a Dose of 4 g/hL (Laboratory Test)

A finished wine from Languedoc Roussillon (Merlot) of vintage 2008 having an initial population level of *Brettanomyces bruxellensis* of $10^5$ cells/mL was treated by adding chitosan of different grain sizes: <25 µm, <50 µm, <90 µm at a dose of 4 g/hL. The control wine does not undergo any treatment.

Figure 3:
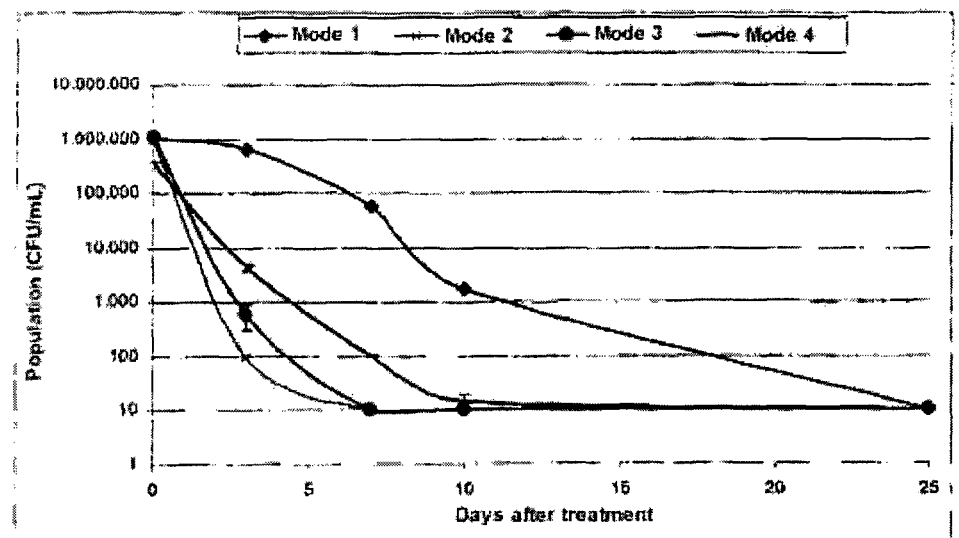
FIG. 3 is a graph tracking the population of *Brettanomyces bruxellensis* in a wine after treatment with chitosan of different grain sizes.

FIG. 3—Tracking the population of *Brettanomyces bruxellensis* in the wine after treatment Caption—
Mode 1: Control;
Mode 2: Treatment with 4 g/hL chitosan—grain size <25 µm;
Mode 3: Treatment with 4 g/hL chitosan—grain size <50 µm;
Mode 4: Treatment with 4 g/hL chitosan—grain size <90 µm After 7 days of treatment, the use of the chitosan with a grain size <25 µm (mode 2) and with a grain size <50 µm (mode 3) generates a reduction in the population of *Brettanomyces bruxellensis* by a factor 5,000 to 10,000 so as to reach the detection threshold (≤10 CFU/mL).

The chitosan having a grain size <90 µm (mode 4) allows a reduction in the population of *Brettanomyces bruxellensis* down to the detection threshold (≤10 CFU/mL) in 10 days, i.e. 3 days more than for the other modes.

Example 5

Treatment of a Red Wine Contaminated by Brettanomyces bruxellensis with Chitosan of Different Degrees of Acetylation at a Dose of 2 g/hL (Laboratory Test)

A finished wine from Languedoc Roussillon (Cabernet Sauvignon) of vintage 2008 having an initial population level of *Brettanomyces bruxellensis* of $5.10^5$ cells/mL was treated by adding chitosan with different degrees of acetylation: 8.5 mol %, 22.0 mol % at a dose of 2 g/hL. The control wine does not undergo any treatment.

Figure 4:
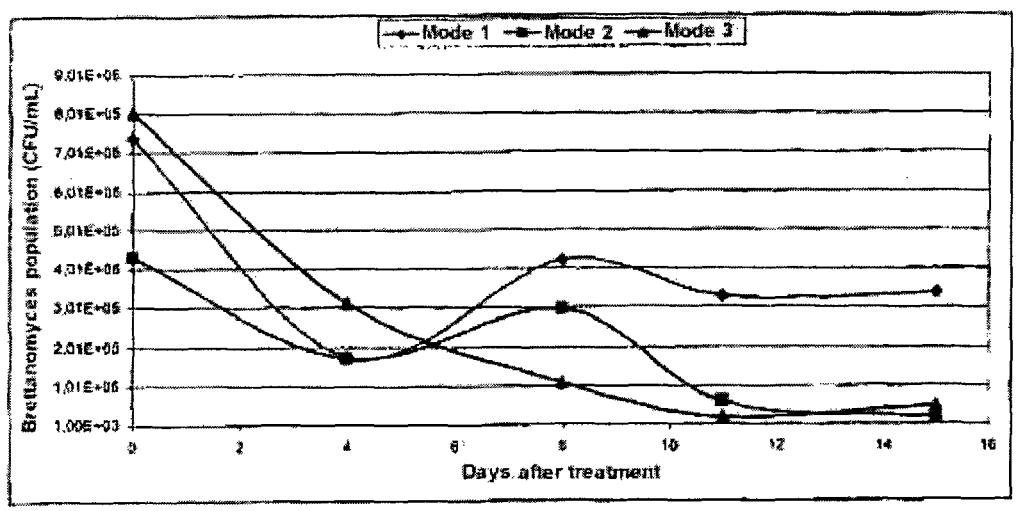
FIG. 4 is a graph tracking the population of *Brettanomyces bruxellensis* in a wine after treatment with chitosan of different degrees of acetylation.

FIG. 4—Tracking the population of *Brettanomyces bruxellensis* in the wines after treatment Caption—
Mode 1: Control;
Mode 2: Treatment with 2 g/hL chitosan—DA 22 mol %;
Mode 3: Treatment with 2 g/hL chitosan—DA 8.5 mol %;

After 11 days of treatment, the use of the chitosan with DA of 22 mol % (mode 2 and with DA of 8.5 mol % (mode 3) generates a reduction in the population of *Brettanomyces bruxellensis* by a factor 100.

Example 6.1

Treatment of a Red Wine Contaminated by Brettanomyces bruxellensis with Chitosan of Different Grain Sizes at a Dose of 4 g/hL (Laboratory Test)

A finished wine from Languedoc Roussillon (Merlot) of vintage 2008 having an initial population level of *Brettanomyces bruxellensis* of $10^5$ cells/mL was treated by adding the chitosan (DA≈8.5 mol %) of different grain sizes: <25 µm, <90 µm at a dose of 4 g/hL. The control wine does not undergo any treatment.

Figure 5A:
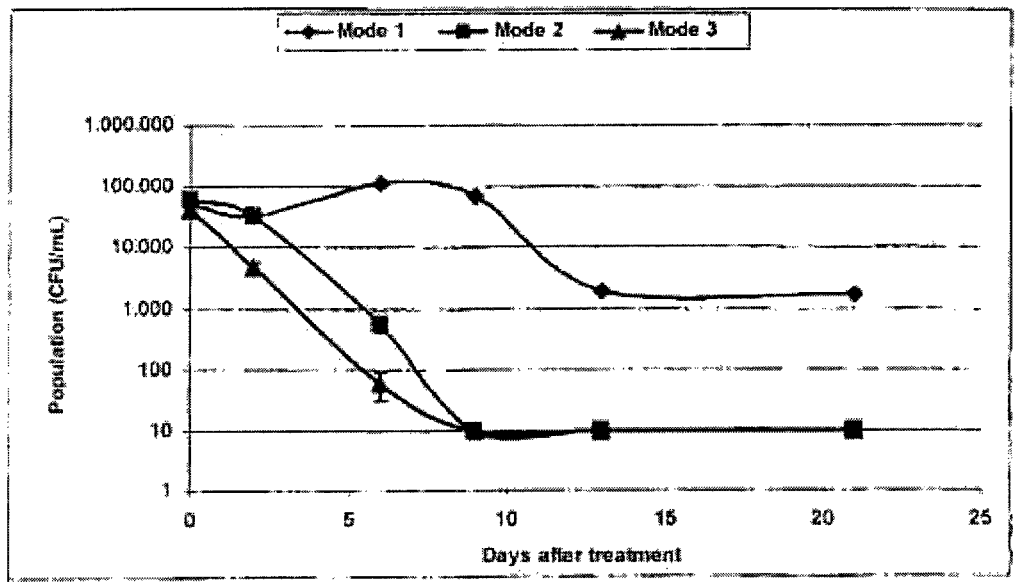
FIG. 5A is a graph tracking the population of *Brettanomyces bruxellensis* in a wine after treatment with chitosan of different grain sizes at a first degree of acetylation.

FIG. 5A Tracking the population of *Brettanomyces bruxellensis* in the wine after treatment Caption—
Mode 1: Control;
Mode 2: Treatment with 4 g/hL chitosan—grain size <25 µm;
Mode 3: Treatment with 4 g/hL chitosan—grain size <90 µm;

After 9 days of treatment, the use of the chitosan batches having a grain size <25 µm (mode 2); <90 µm (mode 3) enabled a drop in the *Brettanomyces bruxellensis* population down to the detection threshold (≤10 CFU/mL) while the untreated control population (mode 1) is maintained during the same time period at its initial level ($10^5$ CFU/mL).

Example 6.2

Treatment of a Red Wine Contaminated by Brettanomyces bruxellensis with Chitosan of Different Grain Sizes at a Dose of 4 g/hL (Laboratory Test)

A finished wine from Languedoc Roussillon (Merlot) of vintage 2008 having an initial population level of *Brettanomyces bruxellensis* of $10^5$ cells/mL was treated by adding chitosan (DA≈22 mol %) of different grain sizes: <25 µm, <90 µm at a dose of 4 g/hL. The control wine does not undergo any treatment.

Figure 5B:
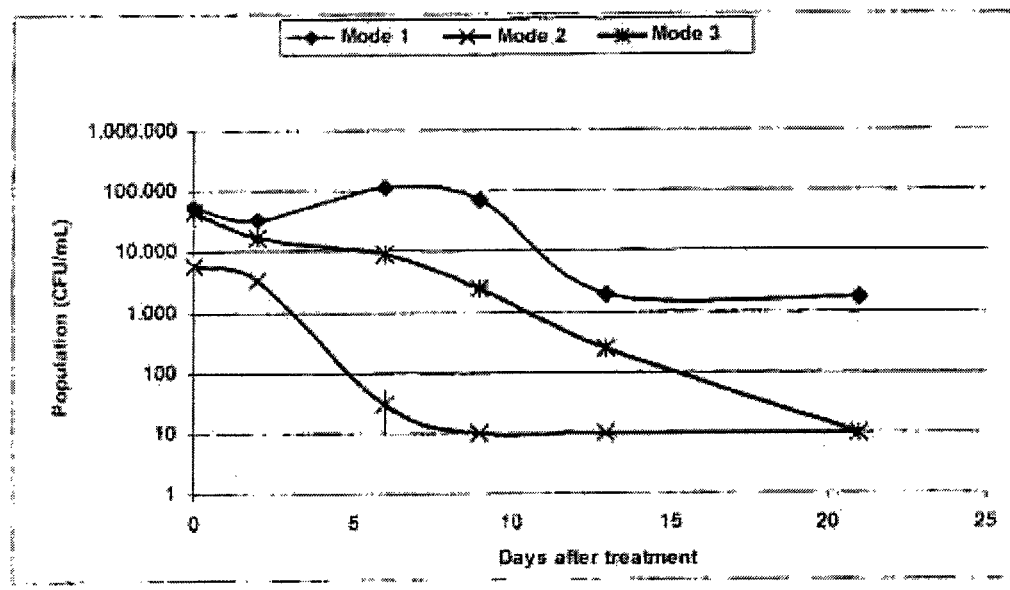
FIG. 5B is a graph tracking the population of *Brettanomyces bruxellensis* in a wine after treatment with chitosan of different grain sizes at a second degree of acetylation.

FIG. 5B—Tracking the population of *Brettanomyces bruxellensis* in the wine after treatment Caption—
Mode 1: Control;
Mode 2: Treatment with 4 g/hL chitosan—grain size <25 µm;
Mode 3: Treatment with 4 g/hL chitosan—grain size <90 µm;

After 9 days of treatment, the use of the chitosan batch having a grain size <25 µm (mode 2) enabled a drop in the population of *Brettanomyces bruxellensis* down to the detection threshold (≤10 CFU/mL) while the population of the untreated control (mode 1) is maintained within the same time period as its initial level ($10^5$ CFU/mL).

The chitosan having a grain size <90 µm (mode 3) enabled a reduction in the population *Brettanomyces bruxellensis* down to the detection threshold (≤10 CFU/mL) in 21 days, i.e. 12 days more than for mode 2.

Example 7

Efficiency of the Treatment with Chitosan at a Dose of 4 g/hL on a Red Wine in which the Implantation Time of *Brettanomyces bruxellensis* is Variable (Laboratory Test)

A finished wine from Languedoc Roussillon (Merlot) with a vintage of 2008 for which the *Brettanomyces bruxellensis* have been implanted in the wine since 3 days or 24 days were treated by adding chitosan at a dose of 4 g/hL.

Figure 6:
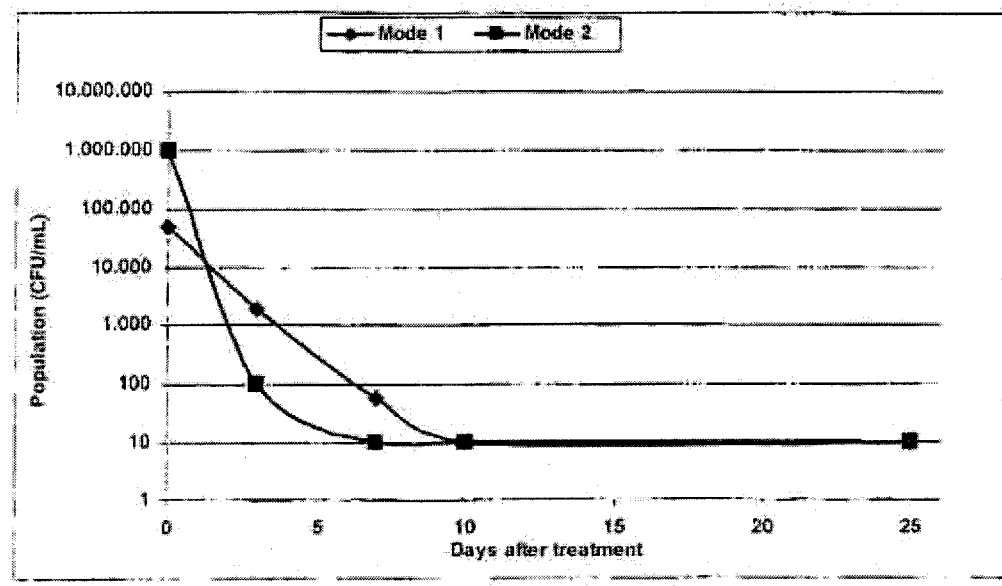
FIG. 6 is a graph tracking the population of *Brettanomyces bruxellensis* in a wine after treatment with chitosan where the implantation time of *Brettanomyces bruxellensis* is variable.

FIG. 6—Tracking the population of *Brettanomyces bruxellensis* in the wine after treatment Caption—

Mode 1: Treatment with 4 g/hL of chitosan on a population of *Brettanomyces bruxellensis* having been implanted since 3 days;

Mode 2: Treatment with 4 g/hL of chitosan on a population of *Brettanomyces bruxellensis* having been implanted since 24 days;

With this example it is possible to demonstrate that the impact of chitosan towards *Brettanomyces bruxellensis* is dependant on their implantation duration in the wine. Thus, the populations of *Brettanomyces bruxellensis* having been implanted since 24 days in the wine (mode 2) are more sensitive to chitosan. After 7 days, the population of *Brettanomyces bruxellensis* has decreased and has attained the detection threshold (≤10 CFU/mL) while 10 days are needed for attaining the same results on a population of *Brettanomyces bruxellensis* having been freshly implanted (mode 1).

Example 8

Impact of the Use of Chitosan at a Dose of 4 g/hL on *Saccharomyces cerevisiae* (Important Yeasts in the Alcoholic Fermentation Process of Wines) (Laboratory Test)

A white grape juice of the Casino brand was supplemented with sugar in order to reach the content of 200 g/L and with nitrogen in order to reach an upper content of 200 mg/L and then inoculated with *Saccharomyces cerevisiae* ICV D47® at a dose of 30 g/hL.

The chitosan was added during alcoholic fermentation at 2 different instants:

density of 1035: 3 days after leavening
density of 1015: 6 days after leavening
The control must does not undergo any treatment.

Figure 7:
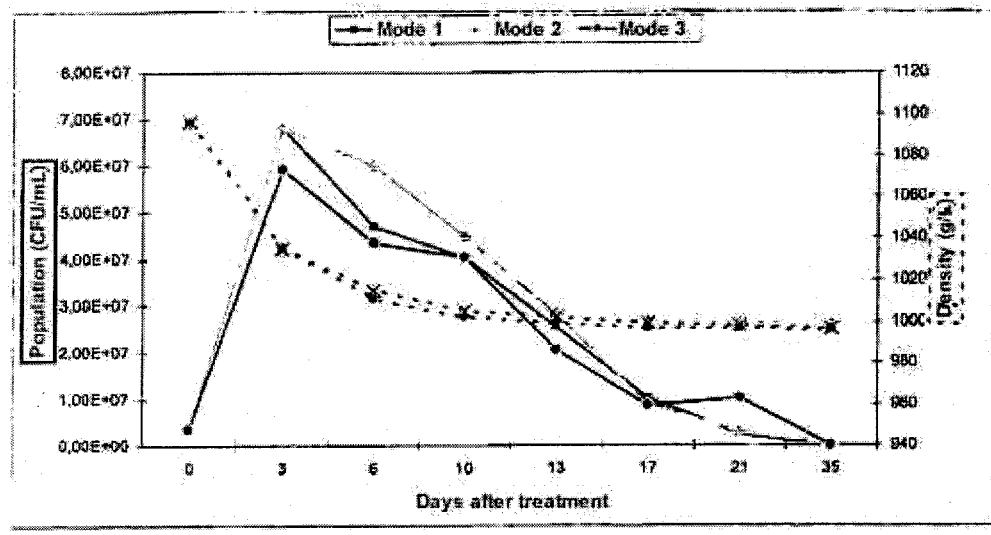
FIG. 7 is a graph illustrating the time-dependent change in population of *Saccharomyces cerevisiae* and tracking the density in must before and after treatment with chitosan.

FIG. 7—Time-dependent change in the population of *Saccharomyces cerevisiae* and tracking the density in the must before and after treatment with chitosan Caption—

Mode 1: Control must

Mode 2: Treatment with 4 g/hL chitosan—3 days after leavening (density 1035);

Mode 3: Treatment with 4 g/hL chitosan—6 days after leavening (density 1031)

The growth kinetics of the population of *Saccharomyces cerevisiae* reaches its maximum value of the order of $6.10^7$ CFU/mL after 3 days of fermentation, and then the number of yeasts is maintained at $5.10^7$ CFU/mL for 10 days in order to finally initiate its decrease phase after 13 days of fermentation. These kinetics are similar for all the modes. Consequently, we may conclude that chitosan does not have any negative impact on the *Saccharomyces cerevisiae* yeasts.

Example 9

Impact of the Use of Chitosan at a Dose of 4 g/hL on *Oenococcus oeni* (Important Bacteria in the Malolactic Fermentation Process of Wines) (Laboratory Test)

A red wine from Languedoc Roussillon (Merlot) of vintage 2008 at the end of alcoholic fermentation was either inoculated with *Oenococcus oeni* Elios 1® or not.

The chitosan was added either within the scope of a malolactic fermentation in a spontaneous mode, or within the scope of a malolactic fermentation by inoculation.

The control wine does not undergo any inoculation with *Oenococcus oeni* or any treatment with chitosan.

Figure 8:
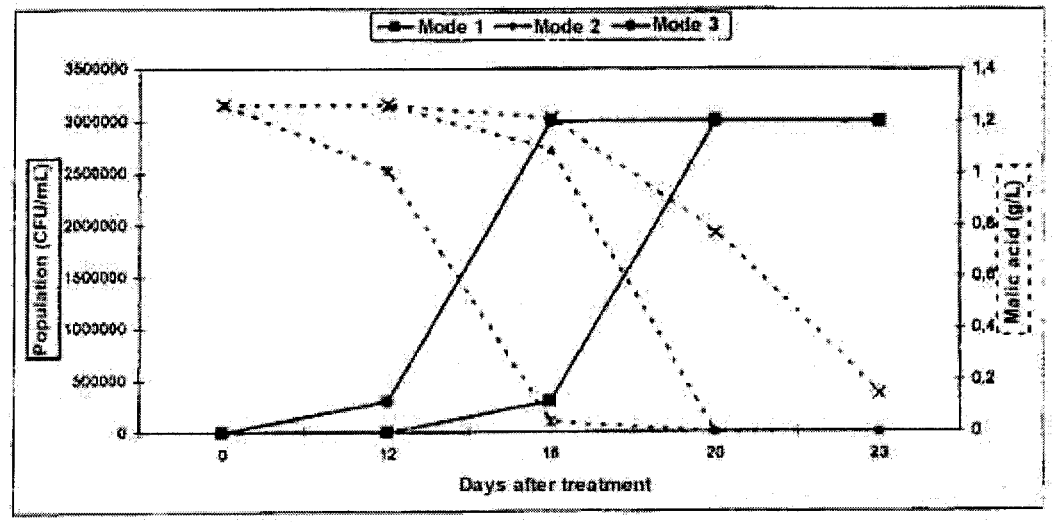
FIG. 8 is a graph illustrating the time-dependent change in population of *Oenococcus oeni* and tracking of malic acid degradation in a wine before and after treatment with chitosan.

FIG. 8—Time-dependent change of the population of *Oenococcus oeni* and tracking of the malic acid degradation in the wine before and after the treatment with chitosan Caption—

Mode 1: Control wine in a spontaneous mode malolactic fermentation—no treatment with chitosan Mode 2: Wine in malolactic fermentation in spontaneous mode—treatment with 4 g/hL chitosan Mode 3: Wine in malolactic fermentation by inoculation—treatment with 4 g/hL chitosan for 8 days before inoculation.

A treatment with chitosan carried out 8 days before the inoculation with lactic bacteria did not have any impact on achieving malolactic fermentation (mode 3).

In the case of spontaneous malolactic fermentation (mode 2), the treatment with chitosan had the effect of extending the latency phase of the malolactic fermentation by 3 days.

As a conclusion, the chitosan had no impact on the course of malolactic fermentation (whether in the spontaneous mode or with inoculation). However, it is recommended to wait for 8 days after the end of the treatment before performing inoculation with lactic bacteria.

Example 10

Treatment of a Red Wine During Alcoholic Fermentation Contaminated by *Brettanomyces bruxellensis* with Chitosan at a Dose of 4 g/hL (a 350 hL Vat)

A red wine during sluggish alcoholic fermentation (Merlot) from cellar C having an initial population level of *Brettanomyces bruxellensis* <10 CFU/mL was treated by adding chitosan at a dose of 4 g/hL. The control wine does not undergo any treatment.

TABLE 4

| | Analytic characteristics of the wine | | | | | | |
|---|---|---|---|---|---|---|---|
| | Sugar (g/L) | TAV (vol %) | Ac.T (g/L $H_2SO_4$) | Active $SO_2f$ (mg/L) | pH | Malic acid (g/L) | Lactic acid (g/L) |
| Before treatment | 12.4 | 14.1 | 4.3 | 0.24 | 3.53 | 1.03 | <0.4 |
| After treatment | 9.9 | 14.26 | 4.39 | 0.19 | 3.55 | 1.03 | <0.4 |

It is noted that chitosan does not modify the conventional analysis parameters after treatment.

TABLE 5

Counting of the initial contamination level of *Brettanomyces bruxellensis* (T0), of its evolution on untreated wine (T7) and the wine treated with chitosan (TR7).

| | Yeasts of the *Brettanomyces* type (CFU/mL) |
|---|---|
| Initial contamination level of the wines (T0) | <10 |
| Contamination level of the control wine after 7 days (T7) | 7 |
| Contamination level of the wine treated with chitosan after 7 days (TR7) | 1.05 |

In this example, the initial contamination level (t0) is low (<10 CFU/mL). However, after 7 days, the population of *Brettanomyces bruxellensis* developed in the untreated sample (T7).

On the other hand, the treatment with chitosan enabled reduction in the population of *Brettanomyces bruxellensis* of the treated sample (TR7).

This example demonstrates that chitosan is efficient for removing *Brettanomyces bruxellensis* on a wine during alcoholic fermentation.

Example 11

Treatment of a Red Wine During Sluggish Malolactic Fermentation, Contaminated by *Brettanomyces bruxellensis*, with Chitosan at a Dose of 4 g/hL (200 hL Vat)

A red wine during malolactic fermentation (Merlot) from the SG cellar having an initial population level of *Brettanomyces bruxellensis* <10 CFU/mL was treated by adding chitosan at a dose of 4 g/hL. The control wine (T7) does not undergo any treatment.

TABLE 6

Analytic characteristics of the wine

| | Sugar (g/L) | TAV (Vol %) | Ac.T (g/L $H_2SO_4$) | Active $SO_2$ (mg/L) | pH | Malic acid (g/L) | Lactic acid (g/L) |
|---|---|---|---|---|---|---|---|
| Before treatment | 9.4 | 13.85 | 4 | 0.39 | 3.65 | 1.33 | 0.6 |
| After treatment | 8.3 | 13.86 | 3.98 | 0.26 | 3.64 | 1.2 | 0.55 |

It is noted that chitosan does not modify the conventional analysis parameters after the treatment.

TABLE 7

Counting of the initial contamination level of *Brettanomyces bruxellensis* (T0), of its development on untreated wine (T7) and on the one treated with chitosan (TR7).

| | Yeasts of the *Brettanomyces* type (CFU/mL) |
|---|---|
| Initial contamination level of the wines (T0) | <10 |
| Contamination level of the control wine after 7 days (T7) | 10 |
| Contamination level of the wine treated with chitosan after 7 days (TR7) | <10 |

In this example, the initial contamination level (T0) is low (<10 CFU/mL). However, after 7 days, the population of *Brettanomyces bruxellensis* developed in the untreated sample (T7).

On the other hand, treatment with chitosan gave the possibility of maintaining the population of *Brettanomyces bruxellensis* below the detection threshold (≤10 CFU/mL).

This example demonstrates that chitosan is efficient for removing *Brettanomyces bruxellensis* on a wine during sluggish malolactic fermentation.

Example 12

Treatment of a Red Wine at the End of Malolactic Fermentation Having Low Contamination by *Brettanomyces bruxellensis*, with Chitosan at a Dose of 4 g/hL, (130 hL Vat)

A red wine at the end of malolactic fermentation (Syrah Carignan Grenache blend) from the MT cellar having an initial population level of *Brettanomyces bruxellensis* of ≤10 CFU/mL was treated by adding chitosan at a dose of 4 g/hL. The control wine (T7) does not undergo any treatment.

TABLE 8

Analytic characteristics of the wine

| | Sugar (g/L) | TAV (vol %) | Ac.T (g/L $H_2SO_4$) | Active $SO_2$ (mg/L) | pH | Malic acid (g/L) | Lactic acid (g/L) |
|---|---|---|---|---|---|---|---|
| Before treatment | 2.95 | 15.29 | 3.27 | 0.25 | 3.65 | <0.3 | 0.85 |
| After treatment | 2.75 | 15.01 | 3.24 | 0.61 | 3.64 | <0.3 | 1 |

It is noted that chitosan does not modify the conventional analysis parameters after treatment.

TABLE 9

Count of the initial contaminated level of *Brettanomyces bruxellensis* (T0), of its development on untreated wine (T7) and on wine treated with chitosan (TR7).

| | Yeasts of the *Brettanomyces* type (CFU/mL |
|---|---|
| Initial contamination level of the wine (T0) | <10 |
| Contamination level of the control wine after 7 days (T7) | 80 |
| Contamination level of the wine treated with chitosan after 7 days (TR7) | 0.04 |

Although the initial contamination level is low (≤10 CFU/mL), the latter develops after 7 days in the control sample. On the other hand, development of *Brettanomyces bruxellensis* was able to be sufficiently stopped in the wine treated with chitosan.

This example demonstrates that chitosan is efficient for removing *Brettanomyces bruxellensis* on a wine at the end of malolactic fermentation, for which the initial population is low.

Example 13

Treatment of a Red Wine at the End of Malolactic Fermentation Having Moderate Contamination by *Brettanomyces bruxellensis* with Chitosan at a Dose of 4 g/hL (45 hL Vat)

A red wine at the end of malolactic fermentation (Syrah Mourvedre Blend) from the MP cellar having an initial population level of *Brettanomyces bruxellensis* of 30 CFU/mL was treated by adding chitosan, at a dose of 4 g/hL. The control wine (T7) does not undergo any treatment.

TABLE 10

Analytic characteristics of the wine

|  | Sugar (g/L) | TAV (vol %) | Ac.T (g/L $H_2SO_4$) | Active $SO_2$ (mg/L) | pH | Malic acid (g/L) | Lactic acid (g/L) |
|---|---|---|---|---|---|---|---|
| Before treatment | 1.8 | 14.39 | 2.97 | 0.15 | 3.75 | <0.3 | 1.4 |
| After treatment | 1.85 | 14.29 | 3.02 | 0.19 | 3.76 | <0.3 | 1.4 |

It is noted that chitosan does not modify the conventional analysis parameters after treatment.

TABLE 11

Count of the initial contamination level of *Brettanomyces bruxellensis* (T0), of its development on untreated wine (T7) and on wine treated with chitosan (TR7).

|  | Yeast of the *Brettanomyces* type (CFU/mL) |
|---|---|
| Initial contamination level of the wine (T0) | 30 |
| Contamination level of the control wine after 7 days (T7) | >3000 |
| Contamination level of the wine treated with chitosan after 7 days (TR7) | <10 |

In spite of a moderate initial contamination level (30 CFU/mL), the latter after 7 days attained a very high level (>3,000 CFU/mL) in the sample which was not treated with chitosan. On the other hand, the sample treated with chitosan has a *Brettanomyces bruxellensis* population of ≤10 CFU/mL.

This example demonstrates that chitosan is efficient for removing *Brettanomyces bruxellensis* on a wine at the end of malolactic fermentation, the initial population of which is moderate.

Example 14

Treatment of a Red Wine at the End of Malolactic Fermentation Having a Strong Contamination by *Brettanomyces bruxellensis*, with Chitosan at a Dose of 4 g/hL (500 hL vat)

A red wine at the end of malolactic fermentation (Syrah) of the R cellar having an initial population level of *Brettanomyces bruxellensis* of 3,400 CFU/mL was treated by adding chitosan, at a dose of 4 g/hL. The control wine (T7) does not undergo any treatment.

TABLE 12

Analytic characteristics of the wine

|  | Sugar (g/L) | TAV (vol %) | Ac.T (g/L $H_2SO_4$) | Active $SO_2$ (mg/L) | pH | Malic acid (g/L) | Lactic acid (g/L) |
|---|---|---|---|---|---|---|---|
| Before treatment | 1.9 | 12.63 | 3.3 | 0.86 | 3.72 | <0.3 | 1.4 |
| After treatment | 1.8 | 12.6 | 3.29 | 0.79 | 3.73 | <0.3 | 1.4 |

It is noted that chitosan does not modify the conventional analysis parameters after the treatment.

TABLE 13

Count of the initial contamination level of *Brettanomyces bruxellensis* (T0), of its development on untreated wine (T7) and on wine treated with chitosan (TR7).

|  | Yeasts of the *Brettanomyces* type (CFU/mL) |
|---|---|
| Initial contamination level of the wine (T0) | 3400 |
| Contamination level of the control wine after 7 days (T7) | >3000 |
| Contamination level of the wine treated with chitosan after 7 days (TR7) | 20 |

It is seen that the treatment with chitosan allows efficient removal of *Brettanomyces bruxellensis* present in the wine. Seven days after treatment, the sample treated with chitosan has a very small population of *Brettanomyces bruxellensis* (<20 CFU/mL) comparatively with the control sample which maintains a high contamination level.

This example demonstrates that the chitosan is efficient for removing *Brettanomyces bruxellensis* on a wine at the end of malolactic fermentation, the initial population of which is high.

Example 15

Treatment of a Red Wine at the End of Malolactic Fermentation Having a Strong Contamination by *Brettanomyces bruxellensis* with Chitosan at a Dose of 4 g/hL (80 hL vat)

A red wine at the end of malolactic fermentation (Syrah, Grenache Blend) from the G cellar having an initial population level of *Brettanomyces bruxellensis* of 1,800 CFU/mL was treated by adding chitosan, at a dose of 4 g/hL. The control wine (T7) does not undergo any treatment.

TABLE 14

Analytic characteristics of the wine

|  | Sugar (g/L) | TAV (Vol %) | Ac.T (g/L $H_2SO_4$) | Active $SO_2$ (mg/L) | pH | Malic acid (g/L) | Lactic acid (g/L) |
|---|---|---|---|---|---|---|---|
| Before treatment | 1.9 | 13.66 | 3.25 | 0.16 | 3.68 | <0.3 | 1.15 |
| After treatment | 2 | 13.73 | 3.26 | 0.16 | 3.67 | <0.3 | 1.15 |

It is noted that chitosan does not modify the conventional analysis parameters after the treatment.

TABLE 15

Count of the initial contamination level of *Brettanomyces bruxellensis* (T0), of its development on untreated wine (T7) and on wine treated with chitosan (TR7).

|  | Yeasts of the *Brettanomyces* type (CFU/mL) |
|---|---|
| Initial contamination level of the wine (T0) | 1800 |
| Contamination level of the control wine after 7 days (T7) | >3000 |
| Contamination level of the wine treated with chitosan after 7 days (TR7)R7) | <10 |

Treatment with chitosan gives the possibility of significantly lowering the population of *Brettanomyces bruxellensis*. The sample treated with chitosan (TR7) has a population of *Brettanomyces bruxellensis* ≤10 CFU/mL comparatively with the untreated sample in which the *Brettanomyces bruxellensis* continued to grow >3,000 CFU/mL.

This example demonstrates that chitosan is efficient for removing *Brettanomyces bruxellensis* on a wine at the end of malolactic fermentation, the initial population of which is high.

Example 16

Treatment of a Cider Contaminated by *Brettanomyces anomalus* with Chitosan at a Dose of 4 g/hL (Laboratory Test)

A commercial cider having an initial population level of *Brettanomyces anomalus* of $10^7$ cells/mL was treated by adding chitosan at a dose of 4 g/hL or by adding DMDC at a dose of 20 g/hL. The control cider does not undergo any treatment.

Figure 9:
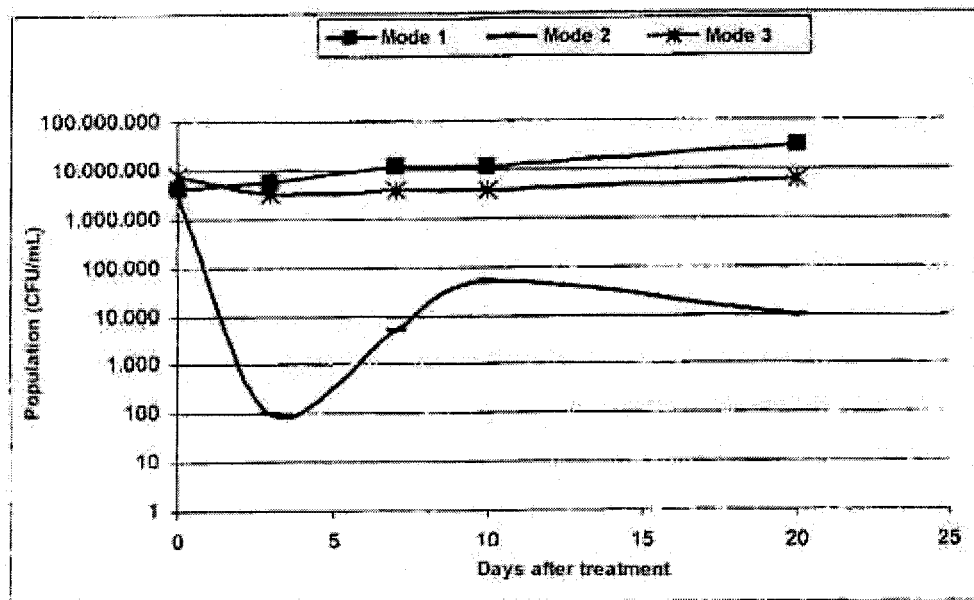
FIG. 9 is a graph tracking the population of *Brettanomyces anomalus* in a cider after treatment with chitosan.

FIG. 9—Tracking the population of *Brettanomyces anomalus* in the cider after treatment.

Caption—

Mode 1: Control;

Mode 2: Treatment with 4 g/hL chitosan

Mode 3: Treatment with 20 g/hL DMDC;

It was seen that only the treatment with chitosan (mode 2) allows a significant reduction in the level of the population of *Brettanomyces anomalus* from $10^7$ CF/mL to 100 CFU./mL in less than 5 days, however after 10 days, the population of *Brettanomyces anomalus* has substantially increased, reaching $5 \cdot 10^4$ CFU/mL The treatment with DMDC (mode 3) has no effect on *Brettanomyces anomalus*.

Example 17

Treatment of a Fruit Juice Contaminated by *Brettanomyces bruxellensis* with Chitosan at Different Doses (Laboratory Test)

A commercial fruit juice (Joker) having a contamination with *Brettanomyces bruxellensis* was treated by adding chitosan (DA≈4.2 mol %) at different doses. The control fruit juice does not undergo any treatment.

After 7 days of treatment, chitosan allows total removal of the *Brettanomyces bruxellensis* presence in the fruit juice.

Example 18

Treatment of a Musk Matrix for Producing Industrial Alcohol, Contaminated by *Brettanomyces bruxellensis* with Chitosan at Different Doses (Laboratory Test)

A must matrix for producing industrial alcohol having a contamination by *Brettanomyces bruxellensis* was treated by adding chitosan (DA≈4.2 mol %) at different doses. The control matrix does not undergo any treatment.

After 7 days of treatment, the chitosan allowed total removal of the *Brettanomyces bruxellensis* present in the industrial must matrix.

Example 19

Treatment of a Red Wine Contaminated by *Brettanomyces bruxellensis* with Chitosan at a Dose of 4 g/hL (Laboratory Test)

A finished Bordeaux wine of vintage 2010 having an initial *Brettanomyces bruxellensis* population level of $1.1 \cdot 10^3$ cells/mL was treated by adding chitosan at a dose of 4 g/hL.

TABLE 16

Tracking the efficiency of the chitosan treatment at a dose of 4 g/hL by quantitative PCR counting and counting on a selective medium.

|  |  | Quantitative PCR counts (CFU/mL) | Selective medium count (CFU/mL) |
|---|---|---|---|
| Bordeaux 2010 | Before treatment | 12,000 | / |
|  | 10 days after treatment | 5,000 | <10 |
|  | 20 days after treatment | 3,300 | <10 |
|  | 30 days after treatment | <10 | <10 |

The results presented in Table 16 show a difference depending on the analysis method: while by cultivation of a gelose medium, a viable population is estimated to be less than 10 colony forming units as soon as the first test (10 days after treatment), it is necessary to wait for 30 days after treatment with the RT-PCR analysis in order to obtain this result.

This will illustrate that chitosan probably interacts with the membrane wall of *Brettanomyces* cells causing destructuration of the latter; this mechanism would induce a response from the cells comparable to a sub-lethal state, preceding their death. In this sub-lethal state, the cells would be identified as viable by quantitative PCR for several days before their total death while analysis on a gelose medium would identify them straightaway as being unable to be cultivated.

Example 20

Treatment of a Red Wine Contaminated by *Brettanomyces bruxellensis* with Chitosan at a Dose of 8 g/hL (Laboratory Test)

A finished wine from the Vallée du Rhône vintage 2009 having an initial population level of *Brettanomyces bruxellensis* of more than $10^3$ cells/l was treated by adding chitosan at a dose of 8 g/hL starting with a 20% suspension.

For this test, the chitosan is weighed and mixed in 5 ml of distilled water (20% mother suspension). 100 μl of this mother suspension are taken and then added to the wine to be treated in an amount of 8 g/hL (by weight of chitosan based on the total liquid volume) for a volume of 250 ml.

TABLE 17

Analytic characteristics of the wine

| Sugar (g/L) | TAV (vol %) | Ac. T (g/L H$_2$SO$_4$) | Active SO$_2$ (mg/L) | pH |
|---|---|---|---|---|
| 1.33 | 13.85 | 2.77 | 0.39 | 3.75 |

TABLE 18

Count on a culture medium of *Brettanomyces bruxellensis* 10 days after treatment

| | Yeasts of the *Brettanomyces* type (CFU/l) |
|---|---|
| Initial contamination level of the wine (T0) | >10,000 |
| Contamination level of the wine treated with chitosan after 10 days (TR10) | <1 |

After 10 days of treatment, the chitosan at a dose of 8 g/hL allows total removal of the *Brettanomyces bruxellensis* present in the wine.

Example 21

Treatment of a Red Wine Contaminated by *Brettanomyces bruxellensis* with Chitosan at a Dose of 4 g/hL (Laboratory Test)

A finished wine from the Vallée du Rhône vintage 2009 having an initial population level of *Brettanomyces bruxellensis* of more than 270 cells/mL was treated by adding chitosan, at a dose of 4 g/hL. starting from a 20% suspension.

For each test, the chitosan is weighed and mixed in 5 ml of distilled water (20% mother suspension). 50 μl of this mother suspension are sampled and then added to the wine to be treated.

TABLE 19

Analytic characteristics of the wine

| Sugar (g/L) | TAV (vol %) | Ac. T (g/L H$_2$SO$_4$) | Active SO$_2$ (mg/L) | pH |
|---|---|---|---|---|
| 1.35 | 13.74 | 2.70 | 0.26 | 3.86 |

TABLE 20

Q-PCR count of *Brettanomyces bruxellensis* 10 days after treatment

| | Yeasts of the *Brettanomyces* type (CFU/mL) |
|---|---|
| Initial contamination level of the wine (T0) | 270 |
| Contamination level of the control wine after 10 days (T10) | Not detected |

After 10 days of treatment, the chitosan at a dose of 4 g/hL allows the total removal of the *Brettanomyces bruxellensis* present in the wine.

Example 22

Treatment of a Red Wine Contaminated by *Brettanomyces bruxellensis* with Chitosan at a Dose of 4 g/hL (Laboratory Test)

A finished wine from Bordeaux vintage 2003 having an initial population level of *Brettanomyces bruxellensis* of $10^5$ cells/mL was treated by adding chitosan at a dose of 4 g/hL. The control wine does not undergo any treatment. The test was duplicated.

TABLE 21

Count of a selective culture medium of populations of cultivatable yeasts in drawn-off wines and logarithmic reduction in the initial population 10 days after treatment.

| | Count of the cultivatable yeasts (CFU/mL) | Logarithmic reduction |
|---|---|---|
| Control (1$^{st}$ repetition) | 6.8 10$^5$ | / |
| Control (2$^{nd}$ repetition) | 5.7 10$^5$ | / |
| 4 g/hL chitosan (1$^{st}$ repetition) | Not detected | Greater than 5 |
| 4 g/hL chitosan (2$^{nd}$ repetition) | Not detected | Greater than 5 |

The results applying the control and shown in Table 21 demonstrate that large populations of *Brettanomyces bruxellensis* persist. On the other hand, in the results of the modes treated with chitosan, it is noted that no population of a cultivatable yeast is detected. The logarithmic reduction is calculated by taking as a reference the cultivatable population present in the wine just before treatment (2.1 10$^5$ CFU/mL). this logarithmic reduction is always greater than 5.

TABLE 22

Count by epifluorescence microscopy of populations of viable and non-viable yeasts performed on lees 10 days after treatment and the percentage of living cells among the lees representing the ratio of the live cells over the totality of the cells counted in the lees.

| | Live cells (cells/mL) | Dead yeasts (cells/mL) | % of live cells among the lees |
|---|---|---|---|
| Control (1$^{st}$ repetition) | 4.8 10$^6$ | No dead yeasts | / |
| Control (2$^{nd}$ repetition) | 8.9 10$^6$ | No dead yeasts | / |
| 4 g/hL chitosan (1$^{st}$ repetition) | 6.1 10$^4$ | 2.4 10$^6$ | 2.5 |
| 4 g/hL chitosan (2$^{nd}$ repetition) | 6.1 10$^4$ | 3.2 10$^6$ | 1.9 |

Analysis of the lees with eipifluorescence microscopy 10 days after treatment (Table 22) demonstrate that in the untreated controls, no dead cell was counted.

On the contrary, in the modes treated with chitosan at a dose of 4 g/hL, a strong proportion of the tested yeasts is dead and the percentage of live yeasts is very low.

Example 23

Treatment of a Red Wine Contaminated by *Brettanomyces bruxellensis* with Different Grain Sizes and Degree of Acetylation (DA) at a Dose of 4 g/hL (Laboratory Test)

A finished wine from Bordeaux vintage 2003 having an initial population level of *Brettanomyces bruxellensis* of $10^5$ cells/mL was treated by adding chitosan with different grain sizes and degree of acetylation: <50 μm, DA=15 (mol %) (Formula A) and <90 μm, DA=15 (mol %) (Formula B) at a dose of 4 g/hL. The control wine does not undergo any treatment. The test was duplicated.

TABLE 23

Count on a selective culture medium of populations of cultivatable yeasts in drawn-off wines and logarithmic reduction in the initial population 10 days after treatment.

|  | Count of cultivatable yeast (CFU/mL) | Logarithmic reduction |
| --- | --- | --- |
| Control (1st repetition) | $6.8 \, 10^5$ | / |
| Control (2nd repetition) | $5.7 \, 10^5$ | / |
| Formula A 4 g/hL (1st repetition) | Not detected | Greater than 5 |
| Formula A 4 g/hL (2nd repetition) | Not detected | Greater than 5 |
| Formula B 4 g/hL (1st repetition) | Not detected | Greater than 5 |
| Formula B 4 g/hL (1st repetition) | Not detected | Greater than 5 |

The results of the controls shown in Table 23 demonstrate that large populations of *Brettanomyces bruxellensis* persist. On the other hand, considering the results of the modes treated with chitosan, it is noted that no cultivatable yeast population is detected. The logarithmic reduction is calculated by taking as a reference the cultivatable population present in the wine just before treatment ($2.1 \, 10^5$ CFU/mL). This logarithmic reduction is always greater than 5.

TABLE 24

Count by epifluorescence microscopy of the viable and non-viable yeast populations carried out on lees, 10 days after the treatment and the percentage of live cells among the lees representing the ratio of the live cells over the totality of the counted cells in the lees.

|  | Live cells (cells/mL) | Dead cells (cells/mL) | % of live cells among the lees |
| --- | --- | --- | --- |
| Control (1st repetition) | $4.8 \, 10^6$ | No dead yeasts | / |
| Control (2nd repetition) | $8.9 \, 10^6$ | No dead yeasts | / |
| Formula A 4 g/hL (1st repetition) | $1.5 \, 10^4$ | $9.1 \, 10^5$ | 1.6 |
| Formula A 4 g/hL (2nd repetition) | $1.5 \, 10^4$ | $1.6 \, 10^6$ | 0.9 |
| Formula B 4 g/hL (1st repetition) | $3.1 \, 10^4$ | $7.0 \, 10^5$ | 4.2 |
| Formula B 4 g/hL (1st repetition) | $6.3 \, 10^4$ | $1.5 \, 10^6$ | 4.0 |

The analysis of the lees by epifluorescence microscopy, 10 days after treatment (Table 24) demonstrates that in the untreated controls, no dead cell is counted.

On the contrary in the modes treated with chitosan at a dose of 4 g/hL, a strong proportion of detected yeasts is dead. The percentage of live yeasts is low regardless of the formula. However it is noted that formula B (grain size <90 μm) has a percentage of live cells greater than that of formula A (grain size <50 μm).

Example 24

Solubility of Chitosan—Purity and Soluble Residues—Dosage by the Method of the Oenological Codex The chitosan according to the invention is practically totally insoluble.

The percentage of insoluble materials should be equal to or greater than 95%. It is determined in the following way (excerpt from the OIV monography of added chitosan of the International Oenological Codex):

Place in solution 5 g of chitosan in 100 mL of bi-distilled water and stir for 2 minutes. Filter after cooling on a tightened filter or on a membrane. Evaporate the filtrate and dry at 100-105° C. The content of soluble materials should not be greater than 5%.

The % of insoluble materials measured on 10 batches of chitosan is transferred into the Table 25 below.

| Batch number of the chitosan | % of insolubles |
| --- | --- |
| 1 | 96.79% |
| 2 | 94.50% |
| 3 | 97.76% |
| 4 | 96.42% |
| 5 | 98.54% |
| 6 | 95.06% |
| 7 | 98.62% |
| 8 | 95.61% |
| 9 | 97.19% |
| 10 | 95.42% |

Example 25

Calculation of the Degree of Crystallinity

The degree of crystallinity of a completely hydrated chitosan according to the invention, is measured by X-ray diffraction. The chitosan powder is hydrated by placing it in an excess of deionized water (10 times its weight) for 24 hours. A diffractometer Siemens D5000 (radiation Cu Kα, 40 kV, 45 mA, variable divergence slots V20, Ni filter+slots of 0.6 mm and 0.2 mm in front of the detector) is used. The data are collected by using a step scan mode from 2 to 60 degrees 2θ at 2.5 sec/step, and a step size of 0.04°.

The degree of crystallinity is calculated by the ratio between the area of the crystalline peaks and the sum of the areas of the crystalline peaks and of the amorphous regions between 7 and 49 degrees 2θ. The reported result is the average of 2 measurements on one batch of chitosan.

TABLE 26

| Degree of crystallinity | |
| --- | --- |
| Before hydration | After hydration |
| 26% | 6% |

Example 26

Dosage of the Residual Chitosan in a Treated Wine

A wine treated with chitosan was filtered on a Buchner by means of a 1 μm Pall type filter. The residue obtained after filtration was then washed with water (Eur.Ph.). The residue present on the filter is then recovered, placed in a flask and washed with water (Eur.Ph) by centrifugation until a measure of conductance of the lower supernatant is obtained at 100 μS. The residue is frozen, freeze-dried and recovered (100 mg). It is suspended in 10 mL of water+50 μl of lactic acid. The sample is then diluted in 1% acetic acid and then injected in HPLC-ELSD i(high performance liquid chromatography coupled with an ELSD (Evaporative Light Scattering Detector) detector) and dosed relatively to calibration with a chitosan standard. The results of the analysis is the following:

Chitosan content in the sample: below the detection limit (10 mg/L).

The invention claimed is:

1. A water-insoluble chitosan in the form of a powder having a grain size comprised between 5 and 50 micrometers (μm), said chitosan comprising a degree of acetylation (DA) comprised between 0 and 30 mol %.

2. A suspension in a liquid of a water-insoluble chitosan, said chitosan being in the form of a powder having a grain size comprised between 5 and 50 micrometers, and said chitosan comprising a degree of acetylation (DA) comprised between 0 and 30 mol %.

3. The suspension according to claim 2, wherein said liquid is water.

4. A method for limiting yeasts of the *Brettanomyces* genus in a fermented liquid food, wherein said method comprises treating said fermented liquid food with an antifungal agent or a composition comprising said antifungal agent, said antifungal agent being a water-insoluble chitosan in the form of a powder having a grain size comprised between 0.1 and 200 micrometers, said chitosan comprising a degree of acetylation (DA) comprised between 0 and 30 mol %, said water-insoluble chitosan being at a concentration from 1 to 10 g/hL of said fermented liquid food to be treated.

5. The method according to claim 4, wherein said chitosan concentration is comprised between 2 and 5 g/hL of said fermented liquid food to be treated.

6. The method according to claim 4, wherein said grain size is comprised between 5 and 50 micrometers.

7. The method according to claim 4, wherein said method is for controlling yeasts of the *Brettanomyces* genus in a fermented liquid food.

8. The method according to claim 7, wherein said yeasts are selected from the group consisting of *Brettanomyces, B. anomalus, B. bruxellensis, B. claussenii, B. custersianus, B. lambicus, B. naardenensis, B. norms*, and any mixtures thereof.

9. The method according to claim 7, wherein said grain size is comprised between 5 and 50 micrometers.

10. A method for controlling undesirable yeasts of the *Brettanomyces* genus in a fermented liquid food of vegetable origin, wherein said method comprises treating said fermented liquid food with an antifungal agent or a composition comprising said antifungal agent, said antifungal agent being a water-insoluble chitosan in the form of a powder having a grain size comprised between 0.1 and 200 micrometers, said water-insoluble chitosan being at a concentration from 1 to 10 g/hL of said fermented liquid food to be treated.

11. The method according to claim 10, wherein said fermented liquid food is selected from the group consisting of a fermented liquid food prepared by fermentation, a wine, a beer, a cider, a sparkling wine, and a fruit juice.

12. The method according to claim 10 wherein said grain size is comprised between 5 and 50 micrometers.

13. A method for curative treatment of a fermented liquid food of vegetable origin in which undesirable yeasts of the *Brettanomyces* genus have to be removed, or the population of undesirable yeasts of the *Brettanomyces* genus has to be limited, said method comprising putting fermented liquid food in the presence with a water-insoluble chitosan or a composition comprising said chitosan, said chitosan being in the form of a powder having a grain size comprised between 0.1 and 200 micrometers, said chitosan being at a concentration from 1 to 10 g/hL of fermented liquid food to be treated.

14. The method according to claim 13, wherein the fermented liquid food is a wine, a beer, or a cider, and wherein undesirable yeasts of the *Brettanomyces* genus are *B. anomalus, B. bruxellensis*, or a mixture of *B. anomalus* and *B. bruxellensis*.

15. The method according to claim 13, wherein said grain size is comprised between 5 and 50 micrometers.

16. The method according to claim 13, wherein said fermented liquid food is a fermented liquid food of vegetable origin prepared by fermentation.

17. The method according to claim 13, wherein said fermented liquid food is put into the presence of chitosan for at least 3 days.

18. The method according to claim 13, wherein said treatment is carried out on fermented liquid food during fermentation.

19. The method according to claim 13, wherein said method comprises putting fermented liquid food in the presence with a water-insoluble chitosan or a composition comprising said water-insoluble chitosan, for a sufficient contact time to remove undesirable yeasts of the *Brettanomyces* genus, or to limit the population of undesirable yeasts of the *Brettanomyces* genus, said chitosan or composition comprising said chitosan being then separated from the fermented liquid food for preserving the fermented liquid food.

20. The chitosan according to claim 1, wherein said water-insoluble chitosan is from *Agaricus bisporus* or *Aspergillus niger*.

21. The suspension according to claim 2, wherein said water-insoluble chitosan is from *Agaricus bisporus* or *Aspergillus niger*.

22. The method according to claim 4, wherein said water-insoluble chitosan is from *Agaricus bisporus* or *Aspergillus niger*.

23. The method according to claim 10, wherein said water-insoluble chitosan is from *Agaricus bisporus* or *Aspergillus niger*.

24. The method according to claim 13, wherein said water-insoluble chitosan is from *Agaricus bisporus* or *Aspergillus niger*.

* * * * *